US006676604B2

United States Patent
Talia et al.

(10) Patent No.: US 6,676,604 B2
(45) Date of Patent: Jan. 13, 2004

(54) METHOD AND APPARATUS FOR PROCESSING ULTRA-SOUND SCANS OF MUSCLES

(76) Inventors: Bartolo Antonio Talia, no. 37/1 Stradello Pirandello, I-41100 Modena (IT); Ferdinando Talia, no. 3 Via Rismondo, I-41100 Modena (IT)

(*) Notice: Subject to any disclaimer, the term of this patent is extended or adjusted under 35 U.S.C. 154(b) by 0 days.

(21) Appl. No.: 10/157,857

(22) Filed: May 31, 2002

(65) Prior Publication Data

US 2003/0060705 A1 Mar. 27, 2003

(30) Foreign Application Priority Data

Sep. 26, 2001 (EP) .............................. 01830606

(51) Int. Cl.⁷ ................................. A61B 8/02
(52) U.S. Cl. ....................................... 600/449
(58) Field of Search ............................. 600/437, 438, 600/439, 440, 441, 442–449, 546, 587, 595; 73/620–630, 602; 367/7, 11, 130, 138; 382/110, 194, 195

(56) References Cited

U.S. PATENT DOCUMENTS 5,806,521 A * 9/1998 Morimoto et al. .......... 600/447
6,099,473 A * 8/2000 Liu et al. .................... 600/449
6,398,736 B1 * 6/2002 Seward ....................... 600/466

* cited by examiner

*Primary Examiner*—Ali M. Imam
(74) *Attorney, Agent, or Firm*—Browdy and Neimark, P.L.L.C.

(57) ABSTRACT

The method of the invention comprises a phase of ultra-sound analysis for creating a sequence of ultra-sound images of a muscle under examination. The sequence of images is directly memorised in an electronic processor which carries out a processing phase of data relating to the sequence of ultra-sound images. The apparatus of the invention uses an ultra-sound apparatus, which collects a sequence of ultra-sound images of the muscle under examination, and an electronic processor which comprises a video card that directly memorises the sequence of ultra-sound images of the muscle under examination obtained by the ultra-sound apparatus. The electronic processor comprises an electronic processing system which directly processes the sequence of images memorised in the processor.

9 Claims, No Drawings

METHOD AND APPARATUS FOR PROCESSING ULTRA-SOUND SCANS OF MUSCLES

BACKGROUND OF THE INVENTION

An evaluation of muscular contraction is one of the vital parameters involved in therapeutic treatment of muscular rehabilitation in the field of traumatic and neurological pathology, as well as in the field of sports therapy and training. Ultra-sound scans have been used for some time now in the medical diagnostic field, as they provide information on the structure of the muscle and its dimensions as well as enabling a visualisation of morphological and dimensional modifications in the muscular venter during the contraction phase. The ultra-sound method used at present, and the relative instruments it is performed with, enable an evaluation of only those morphological modifications of the fibres which take place during contraction. With the ultra-sound apparatus presently available it is not possible to obtain any quantitative information on the contraction dynamics; in other words quantification of the various stages taking place between the start phase (at rest) and the final phase of contraction; nor it is possible to define the parameters of muscular functionality (force, potential, velocity, contraction and relaxation times, etc.), which are important in defining the correct contractile behaviour as well as in identifying where the greatest deficit (if any) takes place within a determined muscular exertion. The latter is necessary so that a suitable therapy cycle or training scheme can be devised.

To obviate this drawback, an apparatus was constructed, object of Italian patent no. IT 1287407, by the present inventor, which, briefly, uses a sampler which, from a pre-selected ultra-sound image of the muscle provided by the apparatus, provides signals which are proportional to the dilation of the section of the muscle under examination and converts them, by means of an analog-digital converter, into digital signals which are then transmitted to a computer. A program then enables the signals relating to a section of muscle, generated analogically and then digitally converted by the sampler, to be processed in a time-dilation diagram which is visualised and memorised.

This apparatus, though obviating the above-mentioned drawbacks, does not enable much and various processing to be carried out on a same section, which would give the advantage of offering a choice to the operator of the best section for the purpose in mind, i.e. the most accurate possible evaluation of a muscular contraction in a single situation.

The prior art teaches another apparatus, US patent U.S. Pat. No. 6,185,451, which analyses the behaviour of the muscles during the performance of certain exercises. This apparatus is limited, however, to an evaluation of the electromyographical changes in the superficial muscles of the pelvis, and can not directly measure the behavior of the deep muscles, only being able to assess their behavior through interpretation of the changes in the electromyographical signals. Further, this apparatus uses signals proportional to the dilation of the surface muscle under examination and converts them, by means of an analog-digital converter, into digital signals which are transmitted to a computer. This apparatus too exhibits the same limits and drawbacks of the previously-described apparatus. The aim of the present invention is thus to provide a method and an apparatus for processing muscular ultrasound readings, which method and apparatus are extremely versatile and able to perform processing operations which are not possible with the apparatus presently available.

The technical characteristics of the invention, in accordance with the above-mentioned aims, are clearly seen from the contents of the claims appended hereto, and the advantages of the invention shall become more evident from the detailed description that follows.

SUMMARY OF THE INVENTION

The main aim of the present invention is to provide a method and apparatus for processing ultra-sound scans of muscles, where the method and apparatus are very versatile; the invention also carries out processing which is not possible with existing apparatus.

DESCRIPTION OF THE PREFERRED EMBODIMENTS

The method and apparatus for processing muscular ultra-sound scans of the invention use an ultra-sound apparatus of known type: using this apparatus a sequence of ultra-sound generated images is composed relating to the muscle being examined. As in the apparatus of Italian patent IT 1287407, with the help of an electronic processor and using a software program, these images are used to generate time-dilation diagrams of the muscle. The method used by the apparatus is, however, different to that used by the above-mentioned known apparatus.

The apparatus in object uses a method involving direct memorisation by the processor of the sequence of ultra-sound images relating to the muscle being examined; for this aim, the apparatus is provided with a video card, of known type, which enables direct memorisation of the ultra-sound images obtained by the ultra-sound machine to be made on the processor.

The sequence of images is memorised by the processor in one or more different formats available in the ultra-sound apparatus. For example, ultrasound images can be presented in monodirectional mode (A-mode, M-mode, continuous doppler, pulse doppler) or in bidirectional mode (B-mode); in scales of grey (for example: B-mode and Doppler PW) and in colour code (e.g. B-mode and ColorDoppler, B-mode and PowerColorDoppler, etc.)

Electronic processing of images is carried out using a known program (for example, similar to the one used in the known apparatus), directly processing the sequence of memorised images in the processor.

Memorising of the images enables considerable apparatus versatility, with the apparatus being able to search and check in ways not available to the above-mentioned known apparatus.

For example, it is possible with the apparatus of the invention to compare the sequence of stored images of the muscle under examination with a sequence of images of previously-examined muscles in order to ascertain directly and automatically the type of muscle presently under examination. Even subsequent to the examination itself (and without the presence of the patient), using this comparison, obtained with an image-comparing system provided on the apparatus, the muscle type can be identified (rectus, pinnate, bipinnate etc.) and, if so desired, compared with muscle response considered as standard, stored in the memory of the apparatus; statistics can also be compiled for that particular type of muscle.

A very interesting capability of the apparatus in object is that it can modify, in relation to the sequence of stored images and therefore after the actual examination, some analytical parameters of the ultra-sound generated image. For example, different portions of the muscular section under examination can be studied but after the examination has been concluded; in this way contractile behaviours could be compared (e.g. the traumatised muscular area is compared to an adjacent non-traumatised zone so that a full cure can be first defined and then planned on the basis of information relating to the non-affected part); also, by calibrating and fine-tuning the software, better evidencing of the desired contraction can be achieved. These capabilities mean that various space-time diagrams of muscular contraction can be compiled, increasing the diagnostic depth of the process.

Thus a series of diagrams can be made up, different among themselves, in order to decide which are the most significant with respect to the research under way; to achieve this result it is not necessary to have the patient present at all times.

It is also worth remembering that, with the process and apparatus in object, it is possible to compare, during data processing and analysis, qualitative (obtained from the image) and quantitative aspects (obtained from the diagrams) of the muscle under examination. This is very important, for example, in diagnosis of traumatic conditions in a muscle, which can be examined visually as well as analytically using the diagrams.

The apparatus also provides means for fixing (various, depending on the muscle being examined: for example, upper limb, lower limb, shoulder, upper and lower back). The means for fixing can concentrate a probe on the section of a muscle under examination. Thus sequences of images of a particular muscle section can be recorded when the patient is actually moving about (training, stress tests, various free-body exercises, exercise bicycles, treadmill and so on)—and variations in muscular contraction at different points of the training procedure can be observed. This can be done in concert with known calibrations of the training machine.

As the processors have large storage capacity, quite long sequences of images can be recorded, advantageous for a subsequent analysis of muscle behaviour. Thus, unlike with known apparatus which only allowed comparison between diagrams obtained from ultra-sound examinations made at various and different times during various training exercises, it is possible to carry out an immediate test of muscle reaction during a lengthy training session. In this way the various responses of the muscle at different moments and at different stress levels during the session can be analysed from recorded data, and important information relating to fatigue and recovery times gleaned therefrom.

Another considerable advantage, with respect to known apparatus, is represented by the fact that the new method, thanks to its greater operational potential, can be used not only for the study of skeletal muscles, but also in examining the heart muscles, namely the walls, which are not at present fully explored with ultra-sound techniques, which are effective only in evaluation of the cardiac valves). The process proposed herein might also be used for all motile organs, where its ability to record over a period of time would be very valuable.

The two apparatus are easily and instantly interfaced, thanks to the direct recording of the sequence of ultra-sound images, in any format in which they are obtained and supplied by the ultra-sound equipment.

Obviously all data pertaining to an examination of a patient and the conditions under which the examination was carried out can be stored in the apparatus' memory. The apparatus also includes a stimulator for producing piloted movement in the muscle, as well as a printer for transferring images and diagrams obtained to paper.

What is claimed:

1. A method for processing ultra-sound scans of muscles, comprising a phase of ultra-sound analysis for creating a sequence of ultra-sound images of a muscle under examination, and a phase of electronic processing of data collected, which data is obtained by means of a processing of images collected during the phase of ultra-sound analysis, for obtaining a time-dilation diagram of the muscle under examination, wherein it also comprises a phase of direct recording onto an electronic processor of the sequence of ultra-sound images of the muscle under examination; the phase electronic processing of data being carried out on the sequence of ultra-sound images.

2. The method of claim 1, comprising at least a phase of comparison between the memorised sequence of ultra-sound images of the muscle under examination and already-memorised standard sequences of images of muscles, with an aim of directly and automatically recognising a type of the muscle under examination.

3. The method of claim 1, wherein the sequence of images is memorised in one or more different imaging formats obtained during the phase of ultrasound analysis.

4. The method of claim 1, wherein the phase of ultra-sound analysis for creating a sequence of ultra-sound images of a muscle under examination is carried out by attaching a probe provided on an ultra-sound apparatus at a position corresponding to a section of muscle to be examined.

5. The method of claim 1, wherein the phase of electronic processing of the sequence of memorised images comprises at least a phase of modification of parameters which are used to effect the analysis of the images for obtaining time-dilation diagrams of the muscle under examination.

6. An apparatus for processing ultrasound scans of muscles, comprising: an ultrasound image collecting apparatus for collecting a sequence of ultrasound images of a muscle under examination while the muscle is alternately contracting and dilating; and an electronic processor which processes data obtained from the ultrasound images of the muscle, providing a time-dilation diagram of the muscle, wherein said processor comprises a video card for receiving and directly memorizing the sequence of ultrasound images of the muscle collected by the ultrasound image collecting apparatus; and an electronic processing system that directly processes the sequence of images memorised in the video card to form the time-dilation diagram.

7. The apparatus of claim 6, wherein the electronic processing system of the electronic processor comprises a system for comparing images which can compare the sequence of memorised images of the muscle under examination with sequences of images of known muscles.

8. The apparatus of claim 6, comprising means for fixing a probe provided on the ultrasound image collecting apparatus at a section of a muscle to be examined.

9. The apparatus of claim 6, wherein the electronic processing system comprises electronic means for modifying parameters, which parameters are used for carrying out an analysis of the images for obtaining time-dilation diagrams of the muscle under examination.

* * * * *